(12) United States Patent
Howell et al.

(10) Patent No.: US 9,183,656 B2
(45) Date of Patent: Nov. 10, 2015

(54) BLEND MODES FOR MINERALOGY IMAGES

(71) Applicant: FEI Company, Hillsboro, OR (US)

(72) Inventors: Garth Howell, McDowall (AU); Michael James Owen, Geebung (AU); Leonardo Salazar, Hamilton (AU); David Haberlah, Salibury (AU); Eric Goergen, Beaverton, OR (US)

(73) Assignee: FEI Company, Hillsboro, OR (US)

( * ) Notice: Subject to any disclaimer, the term of this patent is extended or adjusted under 35 U.S.C. 154(b) by 12 days.

(21) Appl. No.: 14/204,485

(22) Filed: Mar. 11, 2014

(65) Prior Publication Data

US 2015/0262400 A1    Sep. 17, 2015

(51) Int. Cl.
| | |
|---|---|
| *G06K 9/00* | (2006.01) |
| *G06T 11/60* | (2006.01) |
| *G06T 7/40* | (2006.01) |
| *G06T 11/00* | (2006.01) |
| *G01N 23/203* | (2006.01) |

(52) U.S. Cl.
CPC .............. *G06T 11/60* (2013.01); *G01N 23/203* (2013.01); *G06T 7/408* (2013.01); *G06T 11/001* (2013.01); *G06T 2207/20221* (2013.01); *G06T 2207/30181* (2013.01)

(58) Field of Classification Search
USPC ................................................. 382/108, 109
See application file for complete search history.

(56) References Cited

U.S. PATENT DOCUMENTS

| | | | | |
|---|---|---|---|---|
| 5,519,793 | A * | 5/1996 | Grannes ......................... | 382/266 |
| 5,809,177 | A * | 9/1998 | Metcalfe et al. ............... | 382/251 |
| 2003/0205658 | A1* | 11/2003 | Voisin ......................... | 249/187.1 |
| 2003/0235338 | A1* | 12/2003 | Dye ............................. | 382/232 |
| 2005/0259885 | A1* | 11/2005 | Yamazaki ..................... | 382/252 |
| 2010/0128933 | A1* | 5/2010 | Derzhi et al. ................ | 382/109 |

(Continued)

FOREIGN PATENT DOCUMENTS

| | | |
|---|---|---|
| EP | 2546638 | 1/2013 |
| GB | 2223842 A | 4/1990 |
| WO | 9631770 | 10/1996 |

OTHER PUBLICATIONS

Weill, Dan, et al., "Electron Beam MicroAnalysis-Theory and Application", University of Oregon, Department of Geological Sciences and Department of Chemistry, Lecture Notes, Geology 619, Apr. 24, 2013, pp. 1-66, University of Oregon, Eugene, OR.

(Continued)

*Primary Examiner* — Alex Liew
(74) *Attorney, Agent, or Firm* — Scheinberg & Associates, PC; Michael O. Scheinberg (57) ABSTRACT

Optimized blending mode for mineralogy images. A luminosity value is determined for a pixel in a base layer or top layer mineralogy image. An image weighting value is determined from the luminosity value and an optional mixing parameter. A multiply value is determined by multiplying the base and top layer pixel values. An overlay value is determined from twice the multiply value if the value of one of the base layer or top layer pixel values is over a threshold, otherwise it is determined by inverting twice the product of the inverted top layer pixel value with the inverted base layer pixel value. A blended image pixel value is determined by adding the multiply value weighted with the image weighting value and the overlay value weighted with the inverted image weighting value.

22 Claims, 6 Drawing Sheets

(3 of 6 Drawing Sheet(s) Filed in Color)

(56) References Cited

U.S. PATENT DOCUMENTS

| | | | |
|---|---|---|---|
| 2010/0218946 A1* | 9/2010 | Symington et al. | 166/272.6 |
| 2011/0144922 A1 | 6/2011 | Corbett et al. | |
| 2011/0181701 A1* | 7/2011 | Varslot et al. | 348/46 |
| 2012/0033896 A1* | 2/2012 | Barrows | 382/295 |
| 2012/0275658 A1* | 11/2012 | Hurley et al. | 382/109 |
| 2012/0277996 A1* | 11/2012 | Hurley et al. | 702/11 |
| 2013/0094716 A1* | 4/2013 | Carpio et al. | 382/109 |
| 2013/0156270 A1* | 6/2013 | Ellington et al. | 382/109 |
| 2013/0236083 A1* | 9/2013 | Wang et al. | 382/144 |
| 2014/0044315 A1* | 2/2014 | Derzhi et al. | 382/109 |
| 2014/0157870 A1* | 6/2014 | Kornacki et al. | 73/23.38 |
| 2015/0054940 A1* | 2/2015 | Shi et al. | 348/87 |

OTHER PUBLICATIONS

Thomas, Robert, "Photoshop Blend Modes Explained", PhotoBlogStop, Apr. 17, 2001, http://photoblogstop.com/photoshop/photoshop-blend-modes-explained, last access Feb. 26, 2015.

Unknown, http://en.wikipedia.org/wiki/Blend_modes, last accessed Nov. 20, 2013, 5 pages.

"ColorMAP Imaging System", Jan. 1, 2011, 12 pages, <http://www.pointelectronic.de/pdf/manuals/ColorMAP_ohne_Hardware.pdf>.

"Elements Landing Page", Bruker Corporation, Jan. 1, 2015, 3 pages, <https:www.bruker.com/products/x-ray-diffraction-and-elemental-analysis/eds-wds-ebsd-sem-micro-xrf-and-sem-micro-ct/landing-pages/elements-landing-page.html>.

Tobias Salge, "Fast Identification of Mineral Phases: High-Speed Mapping with the XFlash Silicon Drift Detector (SDD), Application Note #EDS-02", Jan. 1, 2011, 2 pages, <https://www.bruker.com/fileadmin/user_upload/8-PDF-Docs/X-ray-Diffraction_ElementalAnalysis/Microanalysis_EBSD/LabReports/App_eds_02_minerals_en_rev1_1_lowres.pdf>.

"ColorMAP—Realtime Processing of 8 Elemental mapping Images and One Analogue Image", Point Electronic, Mar. 10, 2005, 2 pages, <http://www.pointelectronic.de/pdf/ColorMAP_Productsheet.pdf>.

* cited by examiner

BLEND MODES FOR MINERALOGY IMAGES

TECHNICAL FIELD OF THE INVENTION

The present invention relates to the generation and display of mineralogy images, and in particular to a method for automatically blending mineralogy images of a sample, including textural, elemental and spatial mineral identification images.

BACKGROUND OF THE INVENTION

To properly understand and interpret the mineralogy of a sample, knowledge of both the textural information of the sample and the spatial distribution of minerals in the sample is required.

The textural information of a geological sample refers to the size, shape and arrangement of grains or crystals within the sample, the homogeneity of the sample, its degree of isotropy, and the distribution of elements within the minerals The textural information can be measured, for example, by scanning the sample with a high energy beam of charged particles, and measuring at each scanned position the intensity of back-scattered electrons ("BSE's") that are received at an electron detector. The measured BSE intensities are indicators of the average atomic number of elements in the sample as a function of scan position. A plot of the intensity versus scan position can be presented as a grey scale image, where each pixel in the image is a shade of grey that corresponds to the measured BSE intensity at the scanned position. The image so obtained will be darkest where the measured BSE intensity is least, and lightest where the measured BSE intensity is greatest. Of course, this color scheme can be inverted so that the image will be lightest where the measured BSE intensity is least, and darkest where the measured BSE intensity is greatest.

In addition to BSE intensity, other forms of textural information can include representation of the rate of x-ray production at each pixel. This is measured by scanning the sample with a high energy beam of charged particles, and measuring the intensity of x-rays produced by the sample and received by an x-ray detector. The x-rays are produced when the charged particles dislodge electrons in the sample, and electrons from higher energy shells fall into the energy shells vacated by the dislodged electrons. The rate at which the x-rays are produced is roughly proportional to the volume and atomic number of the material in the sample. A plot of the x-ray generation rate versus scan position can be presented as a grey scale image, where each pixel in the image is a shade of grey corresponding to the measured rate of x-ray production at each scan position. The image so obtained will be darkest where the measured x-ray production rate is lowest, and brightest where the measured x-ray production rate is highest.

The spatial distribution of minerals in the sample is a plot of the minerals identified in the sample as a function of sample position. It can be generated by scanning the sample with a high energy beam, and measuring the energy distribution of x-rays emitted from the sample as a function of scan position. On a per pixel basis, these energy distributions can be fitted and/or compared to a catalog of energy distributions obtained from pure elements or pure minerals in order to identify the elements and/or minerals in the sample at each scanned position. Techniques for identifying minerals based on a catalog of elemental x-ray spectra are disclosed, for example, in U.S. patent application Ser. No. 12/866,697, filed on Feb. 6, 2009, which is herein incorporated by reference in its entirety. Techniques for identifying minerals based on a catalog of mineral x-ray spectra are disclosed, for example, in U.S. patent application Ser. No. 14/073,523, filed on Nov. 6, 2013, which is herein incorporated by reference in its entirety. Different colors can be assigned to different minerals in the catalog, and an image of the spatial mineral distribution in the sample can be generated by plotting the colors of identified minerals as a function of scanned position.

Since proper understanding of the mineralogy of a sample requires knowledge of both the textural information of the sample and the spatial distribution of minerals in the sample, methods are needed to combine the textural and spatial mineral distribution images into a single composite image that reveals both the spatial mineral distribution and textural information about the sample.

SUMMARY OF THE INVENTION

An object of the invention is to provide an automated mechanism to allow data from multiple detectors to be simultaneously visualized without losing information from either data source.

In one aspect, the invention features a computer implemented method for blending mineralogy images, including a base layer mineralogy image and a top layer mineralogy image. For each pixel in the base or top layer mineralogy images a base layer value is determined from the pixel in the base layer mineralogy image, and a top layer value is determined from the pixel in the top layer mineralogy image. A luminosity value is determined from one of the base layer or top layer values. A multiply value is determined by multiplying the base and top layer values. An overlay value is determined by doubling the multiply value if one of the base layer or top layer values is less than a threshold, and by otherwise inverting twice the product of the inverted top layer value with the inverted bottom layer value. An image blending weight is determined from the luminosity value. A blended image value is determined as a weighted average of the multiply value and the overlay value, wherein the multiply value is weighted by the image blending weight and the overlay value is weighted by the inverted image blending weight.

Implementations of the invention may include one or more of the following features. The base layer mineralogy image can be a textural mineralogy image and the top layer mineralogy image can be a spatial mineral distribution image. The textural mineralogy image can be an image of the intensity of back-scattered electrons or an image of the intensity of generated x-rays. The image blending weight can be determined by multiplying the luminosity value by a mixing parameter. A blended image, where each pixel of the blended image has a blended image value determined from the base layer value and top layer value, can be displayed on a display device.

In another aspect, the invention features a computer implemented method for blending mineralogy images of a sample, including an elemental distribution image of the sample, and a mineral distribution image of the sample. A blended image of the sample can be generated by blending the elemental and mineral distribution images of the sample.

Implementations of the invention may include one or more of the following features. Each pixel in the blended image of the sample can be generated from each pixel in the elemental and mineral distribution images. A base layer value can be determined from the pixel in the elemental distribution image. A top layer value can be determined from the pixel in the mineral distribution image. A luminosity value can be determined from one of the base layer or top layer values. A multiply value can be determined by multiplying the base and top layer values. An overlay value can be determined by doubling the multiply value if one of the base layer or top layer values is less than a threshold, and by otherwise inverting twice the product of the inverted top layer value with the inverted bottom layer value. An image blending weight can be determined from the luminosity value. A blended image value can be determined as a weighted average of the multiply value and the overlay value, wherein the multiply value is weighted by the image blending weight and the overlay value is weighted by the inverted image blending weight. The image blending weight can be determined by multiplying the luminosity value by a mixing parameter.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

Implementations of the invention may also include one or more of the following features. Each pixel in the blended image of the sample can be generated by determining a top layer value from the pixel in the mineral distribution image, determining an opacity value from the pixel in the elemental distribution image; and alpha blending the top layer value with a black pixel value using the opacity value. The pixel in the blended image can be rendered black when the corresponding pixel in the elemental distribution image has a value that is less than an elemental threshold.

BRIEF DESCRIPTION OF THE DRAWINGS

The patent or application file contains at least one drawing executed in color. Copies of this patent or patent application publication with color drawings will be provided by the Office upon request and payment of the necessary fee. For a more thorough understanding of the present invention, and advantages thereof, reference is now made to the following descriptions taken in conjunction with the accompanying drawings, in which.

DETAILED DESCRIPTION OF PREFERRED EMBODIMENTS

Proper understanding of the mineralogy of a sample requires knowledge of both the texture of the sample and the spatial distribution of minerals in the sample. Methods are disclosed for forming a blended image by combining textural and spatial mineral distribution images of a sample to facilitate an understanding of its mineralogy. In one embodiment, the two images can be blended together using known image blending techniques, such as by compositing the two images as layers in a blended image. The degree of blending can be controlled by assigning a global opacity value to the alpha channel of the spatial mineral distribution image. The textural and spatial mineral distribution images can then be blended using a conventional alpha blending algorithm. This approach, however, tends to wash out the colors in the spatial mineral distribution layer.

Other image blending techniques from the image processing arts can be used to combine the textural and spatial mineral distribution images. For example, the color values of pixels in the textural and spatial mineral distribution images can be added together, subtracted, multiplied or divided by one another to obtain the color values of corresponding pixels in the blended image. Since each of these image blending techniques is globally applied (i.e., identically applied to each pixel in the blended image), each technique produces a global effect on the blended image. For example, multiplying images creates a blended image that is everywhere darker than either of the combined images, while dividing images creates a blended image that is everywhere lighter than either of the combined images.

Some image blending modes address these global compositing issues by thresholding the image compositing function. That is, different image compositing functions are used depending on whether the color value in one of the layers to be blended exceeds a threshold. Examples of such blending modes include the overlay, hard light, and soft light blending. However, depending on the threshold selected, portions of the image far from the threshold may appear too dark or too light.

To optimize the information presented in a blended image consisting of textural and spatial mineral distribution images from a sample, a custom blending method has been developed. This method combines elements from conventional multiply, screen and overlay blending modes, and mixes these modes on a per pixel basis as a function of the luminosity of the pixel color in the textural or spatial mineral distribution images.

Figure 1:
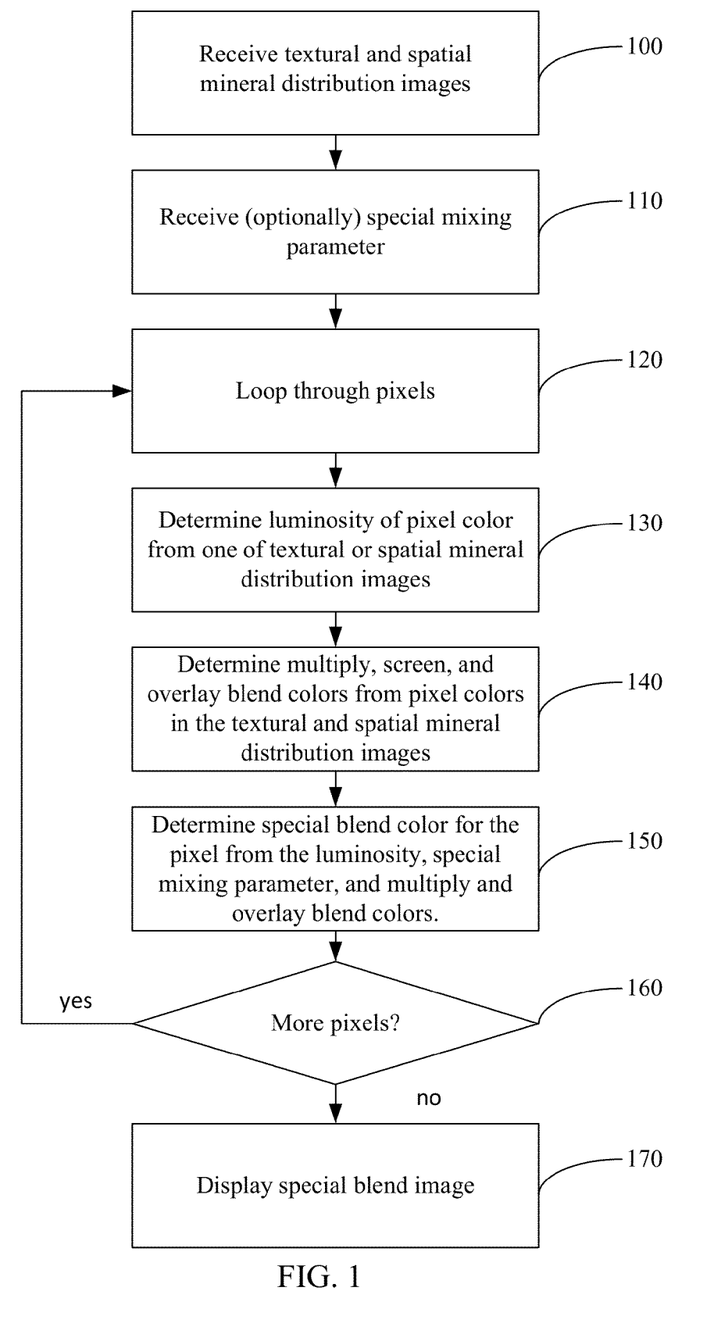
FIG. 1 is a flow chart depicting a method for blending textural and spatial mineral distribution images.

FIG. 1 is a flow chart depicting a method for blending textural and spatial mineral distribution images. The method begins by receiving a textural image and a spatial mineral distribution image for a sample (100). In one implementation, an optional mixing parameter k that ranges in value between 0 and 1 is also received (110). In some implementations, the mixing parameter k can be received from a computer memory, where it is set to a default value such as 0.6. In other implementations, the mixing parameter can be received as user input, e.g., from a text box or as a radio button selection in a graphical user interface presented to the user. Setting the mixing parameter k to a default value of 1 is equivalent to having no mixing parameter at all, as further explained below.

The method proceeds by looping through all of the pixels in the textural and spatial mineral distribution images (120). If the images have different resolutions, one or both images can be renormalized so they have the same resolution or number of pixels. For each pixel, the luminance of the color in either the textural or the spatial mineral distribution image is determined (130). For example, in one implementation, the luminance of the textural image is determined. If this distribution is a grey scale image (e.g., representing the intensity of BSE's), the luminance is simply the grey value for that pixel. In another implementation, the luminance of the spatial mineral distribution image is determined. If the pixel color in the spatial mineral distribution image is stored in the RGB or red, green, blue color space, the luminance Y can be determined as:

$$Y=0.299R+0.587G+0.114B \quad \text{(Eq.1)}$$

If the pixel color is stored in other color spaces, well known formulas can be used to determine the luminance from the pixel's color values in those color spaces. By normalization, the luminance lies within a range of 0 to 1.

Next, pixel values for the conventional multiply, screen and overlay blending modes are obtained from the pixel values of the textural and spatial mineral distribution images. The multiply blend value is simply the product of the pixel values from these two images:

$$M_{ij}(l)=T_{ij}(l)*SMD_{ij}(l) \quad \text{(Eq. 2)}$$

where $M_{ij}$, $T_{ij}(l)$, and $SMD_{ij}(l)$ are respectively the multiply blend value, the textural image value, and the spatial mineral distribution image value for the lth color component of pixel (i,j). The pixel value in the multiply blend will be darker than the pixel values in either the textural or spatial mineral distribution images. This mode is therefore useful for blending high intensity areas of the textural and spatial mineral distribution images; however, low intensity areas often come out too dark to provide useful information about the mineralogy of the sample. The screen blend pixel value $SCR_{ij}(l)$ is obtained by inverting the product of the inverted pixel values from the textural and spatial mineral distribution images. It can be computed as:

$$SCR_{ij}(l)=1-(1-T_{ij}(l))*(1-SMD_{ij}(l)) \quad \text{(Eq. 3)}$$

The pixel value in the screen blend will be lighter than the pixel values in either the textural or spatial mineral distribution images. This mode is therefore useful for low intensity areas of the textural and spatial mineral distribution images; however, high intensity areas often come out too light to provide useful information about the mineralogy of the sample. Finally, the overlay blend value $O_{ij}(l)$ can be computed as:

$$O_{ij}(l) = \begin{cases} M_{ij}(l) & \text{if } SMD_{ij}(l) < 0.5 \\ SCR_{ij}(l) & \text{otherwise} \end{cases} \quad \text{(Eq. 4)}$$

The overlay blend mode attempts to address the shortcomings in the multiply and screen blend modes when dealing with very bright or dark compositing layers by selecting the multiply mode if the pixel value is less than a threshold and the screen mode if the pixel value is greater than the threshold.

Next, a special blend value is calculated for the pixel in the blended image from the multiply and overlay pixel values, the mixing parameter k, and the luminosity of the pixel color in either the textural or the spatial mineral distribution image. The special blend value is computed as a weighted average of the multiply and overlay pixel values, where the weights are determined by the product r=k*Y, where k is the optional mixing parameter and Y is the luminosity of the pixel color in the textural or spatial mineral distribution image. Thus, the special blend $SB_{ij}(l)$ value of the pixel is given by:

$$SB_{ij}(l)=rM_{ij}(l)+(1-r)O_{ij}(l) \quad \text{(Eq. 5)}$$

Since both the mixing parameter k and the pixel intensity Y are normalized to lie in the range of 0 to 1, the weight r also lies in the range of 0 to 1. Note that when the special mixing parameter k=1, the weight r reduces to the luminosity Y as if there were no mixing parameter k.

As a weighted average, the special blend provides for continuous blending of the textural and spatial mineral distribution images, with no thresholding. It produces a blended image that is optimized for both low and high luminosity areas in the spatial mineral distribution image, when blended with both low and high luminosity areas in the textural image. High intensity colors in the spatial mineral distribution image (e.g., bright reds and yellows) retain their chrominance in the blended image and are easily discernible, even when blended with high intensity areas of the textural image. Moreover, high intensity colors in the spatial mineral distribution image retain their luminance in the blended image, even when blended with low intensity areas of the textural image.

Figure 2A:
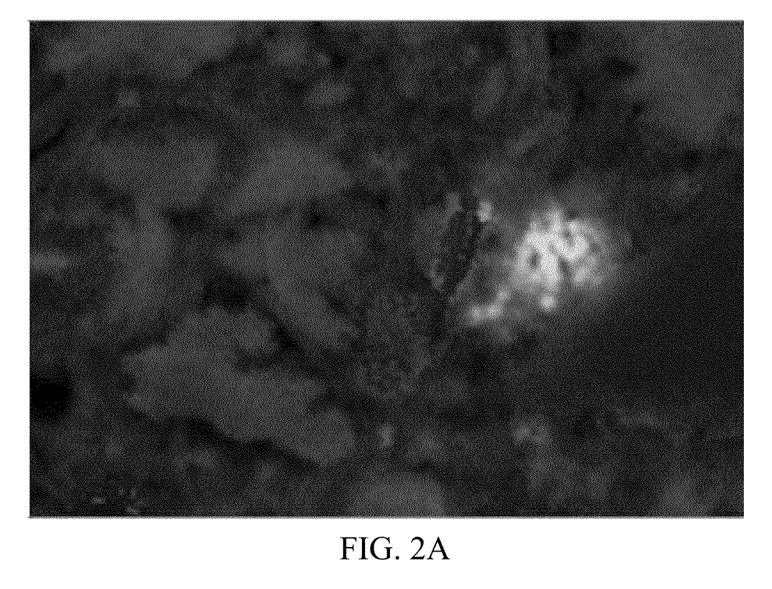
FIG. 2A is an illustration of a blended image made by blending a textural image with a spatial mineral distribution image using the multiply blend mode.

FIG. 2A is an illustration of a blended image made by blending a textural image with a spatial mineral distribution image using the multiply blend mode. The blended textural and spatial mineral distribution images were made for a sample containing the minerals pyrite (bright yellow) and rutile (red). As seen in the illustration, while the multiply blend image preservers the colors of the pyrite and rutile minerals, it is everywhere else too dark, and fails to preserve useful information from the textural and the spatial mineral distribution images.

Figure 2B:
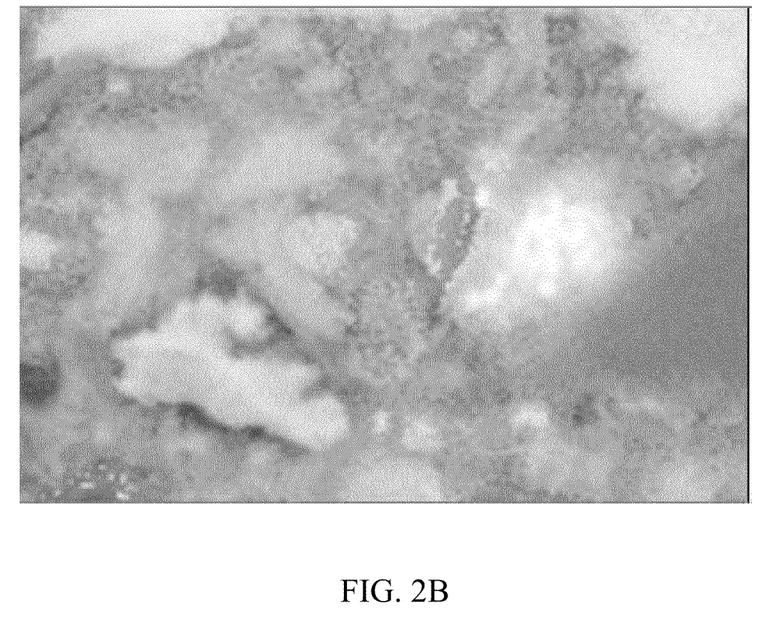
FIG. 2B is an illustration of a blended image made by blending a textural image with a spatial mineral distribution image using the multiply blend mode.

FIG. 2B is an illustration of a blended image made by blending a textural image with a spatial mineral distribution image using the screen blend mode. As seen in the illustration, the screen blend image is lighter than the multiply blend image shown in FIG. 2A. As a result, more information from both the textural and spatial mineral distribution images is revealed. Nonetheless, the high luminosity colors for pyrite and rutile are significantly faded, resulting in a loss of information from the spatial mineral distribution image.

Figure 2C:
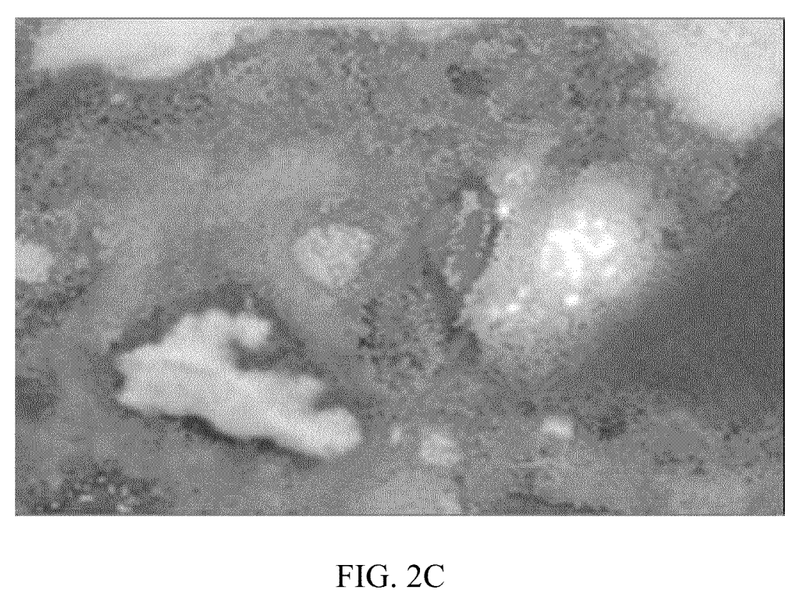
FIG. 2C is an illustration of a blended image made by blending a textural image with a spatial mineral distribution image using the overlay blend mode.

FIG. 2C is an illustration of a blended image made by blending a textural image with a spatial mineral distribution image using the overlay blend mode. As seen in the illustration, the overlay blend image is lighter than the multiply blend image shown in FIG. 2A, but darker than the screen blend image shown in FIG. 2B. As a result, more information from both the textural and spatial mineral distribution images is revealed in the overlay blended image. Nonetheless, the high luminosity colors for pyrite and rutile remain faded in the blended image, resulting in a loss of information from the spatial mineral distribution image.

Figure 2D:
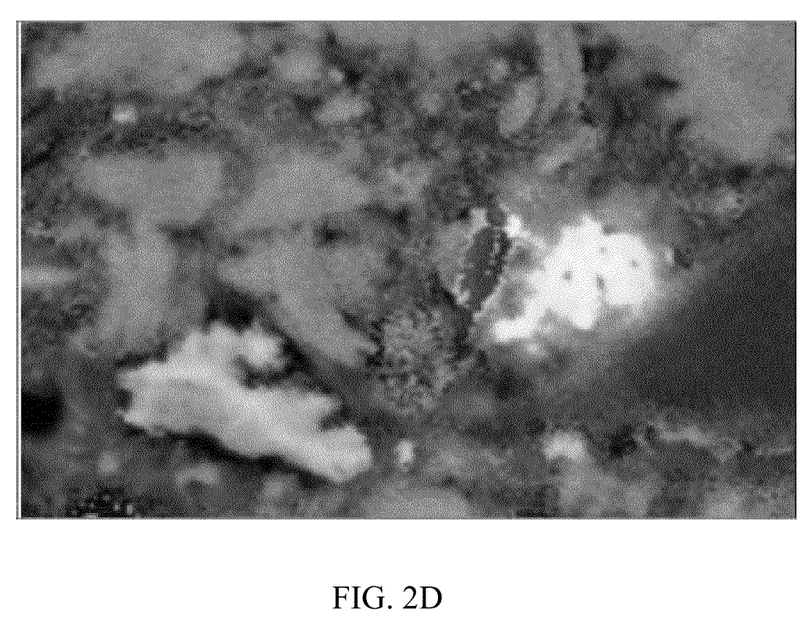
FIG. 2D is an illustration of a blended image made by blending a textural image with a spatial mineral distribution image using the special blend mode.

FIG. 2D is an illustration of a blended image made by blending a textural image with a spatial mineral distribution image using the special blend mode. As seen in the illustration, the special blend image is lighter than the multiply blend image shown in FIG. 2A, but darker than the overlay blend image shown in FIG. 2C. As a result, more information from both the textural and spatial mineral distribution images is revealed. Moreover, the high luminosity colors for pyrite and rutile continue to stand out in the special blend image, preserving information about these minerals in the sample recorded in the spatial mineral distribution image The methods disclosed herein can be used to blend any type of textural and spatial mineral distribution information. In some embodiments, the textural image can be a per pixel record of the total number of x-rays emitted by the sample at the pixel scan position. In this embodiment, the blended image can provide a user with information regarding confidence in the mineral identification for the sample. For example, if a sample's spatial mineral distribution image contained a large monotone red area (indicating the identification of rutile in some area of the sample), and the sample's textural image (composed of per-pixel x-ray counts) showed large counts in the center of the red area but smaller counts toward its edges, the corresponding area in the blended image would be different shades of red corresponding to the different x-ray pixel counts in the textural image. Where the x-ray count is larger (e.g., in the center), the red in the blended image would be a brighter shade than in those areas where the x-ray count is smaller (e.g., along the edges). Since the likelihood of correctly identifying a mineral is proportional to the x-ray count, areas of the blended image having a brighter shade of a pure mineral color (e.g., red, blue) will be areas of higher mineral identification confidence, while areas of the blended image having a darker shade of a pure mineral color will be areas of lower mineral identification confidence.

Figure 3:
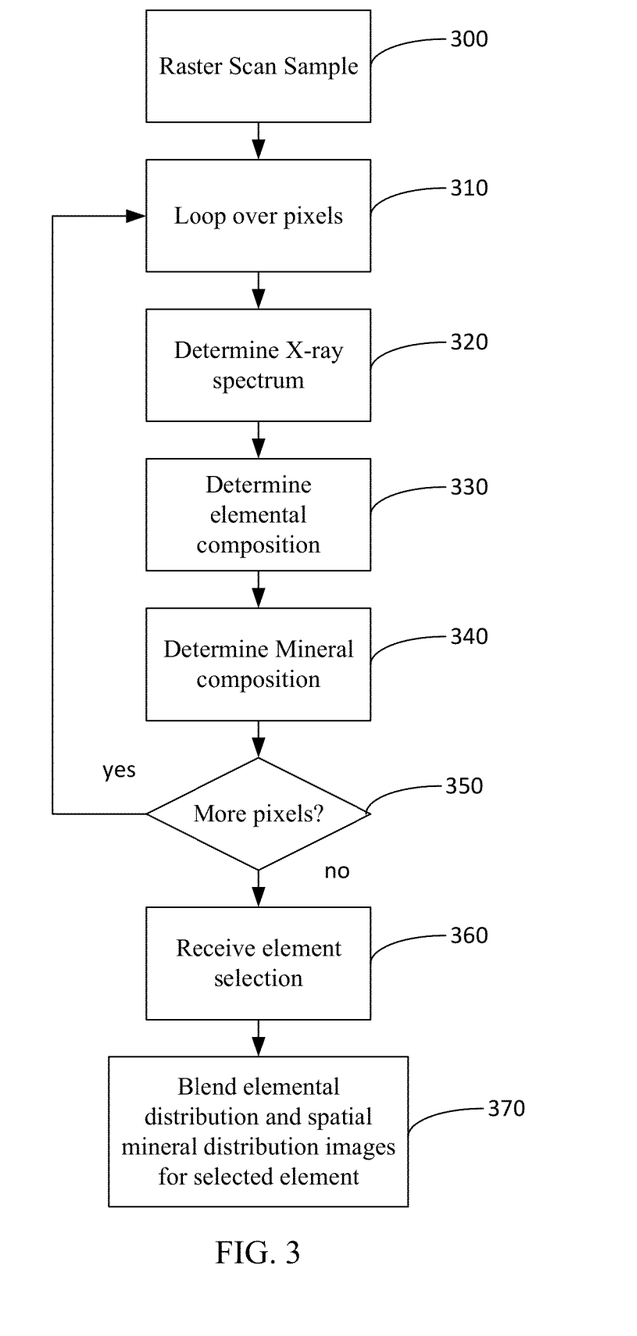
FIG. 3 is a flow chart depicting a method for blending an elemental distribution image and a spatial mineral distribution image.

FIG. 3 is a flow chart depicting, in yet another embodiment of the invention, a method for blending elemental and mineral distribution images. Both the elemental distribution image and the mineral distribution image can be obtained by analyzing, on a per pixel basis, the energy distribution of x-rays emitted from a sample when bombarded with charged particles. As shown in FIG. 3, the process begins by raster scanning the sample (300). Next, for each pixel in the image (310), an x-ray emission spectrum is obtained (320). This sample x-ray emission spectrum is then analyzed to determine both the elemental (330) and the mineral (340) composition of the sample at the pixel scan position. This process is repeated (350), for all pixels or scan positions for the sample.

As disclosed in U.S. patent application Ser. No. 12/866, 697, filed on Feb. 6, 2009, which is herein incorporated by reference, the elemental distribution image for the sample can be obtained by fitting, on a per pixel basis, the sample's x-ray emission spectrum with elemental x-ray emission spectra to determine the number, kind, and percentage of elements present in the sample. The elemental composition so determined can then be used to determine the mineral composition and the mineral distribution of the sample. Moreover, for each element present in the sample, an elemental distribution image can be generated by assigning a grayscale value to each pixel in the image corresponding to the percentage of the element found in the sample at that pixel location or scan position.

As disclosed in U.S. patent application Ser. No. 14/073, 523, filed on Nov. 6, 2013, which is herein incorporated by reference in its entirety, the spatial mineral distribution image for the sample can also be obtained by fitting, on a per pixel basis, the sample's x-ray emission spectra with mineral x-ray emission spectra to determine the number, kind, and percentage of minerals present in the sample. Each mineral determined to be present in the sample can be assigned a color, and when more than one mineral is present the colors can be blended together, with the amount of blend determined by the percentage of mineral present in the sample.

Referring again to FIG. 3, once the elemental and mineral distribution images are obtained, an elemental selection can be received. For example, the process can present a user with a list of elements and minerals identified in the sample, and with the percentages of each. The user can then select a particular element for forming a blended image. For example, the user can select the element by entering its name in a text box, or by selecting a radio button or check box associated with the element in a graphical user interface. Once selected, the elemental distribution image and the mineral distribution image can be combined.

In one embodiment, the elemental and mineral distribution images can be combined using the special blend mode discussed above in reference to FIG. 1. In other embodiments, the elemental and mineral distribution images can be combined using any conventional image blending function. For example, the grayscale value recorded in the elemental distribution image can be used to determine the opacity of the mineral distribution image. In this way, the blended image will only contain areas of the mineral distribution image that overlap with areas in the elemental distribution image. All other areas of the blended image will appear black. Moreover, the shades of colors assigned to minerals identified in the mineral distribution image will vary in the blended image depending on the percentage of the selected element found in the elemental distribution image. Identified mineral colors in the blended image will be brightest in those areas corresponding to elemental distribution image areas having a high percentage of the selected element, and darkest in those areas corresponding to elemental distribution image areas having a low percentage of the selected element.

In some embodiments, when an element selection is received in step 360, an elemental threshold can be optionally received. In these embodiments, pixels in the elemental distribution image will only be blended with pixels in the mineral distribution image if they are above the elemental threshold. For example, if the received elemental threshold is 12%, the blended image will only contain pixels in the mineral distribution image blended with pixels in the elemental distribution image that have a grayscale value greater than 0.12. Pixels in the elemental distribution image having a grayscale value less than 0.12 will appear black in the blended image. In this way, regions of interest, defined as regions having an elemental composition greater than a specified threshold value, can be easily defined and displayed.

Figure 4:
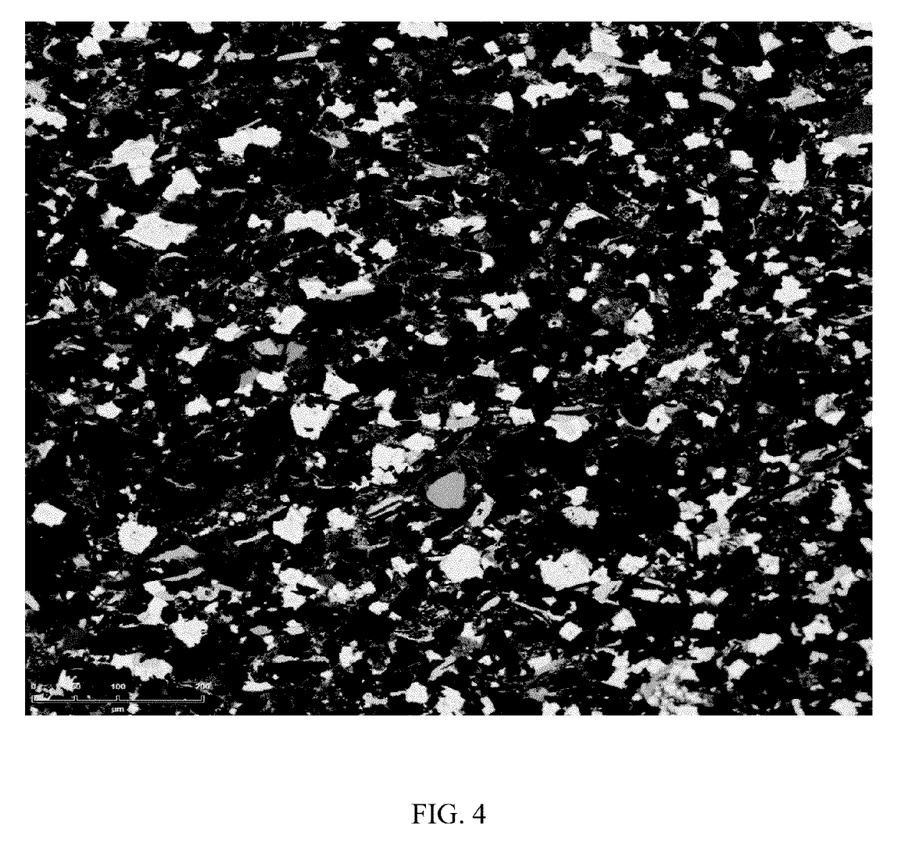
FIG. 4 is an illustration of a blended image made by blending an elemental distribution image with a spatial mineral distribution image.

FIG. 4 is an illustration of a blended image made by blending an elemental distribution image with a mineral distribution image. In FIG. 4, the selected element is magnesium (Mg), and the blended image shows areas of a sample where Mg is present in either dolomite (blue) or clay (green). As seen from the image, different shades of green indicate areas containing clays (identified in the mineral distribution image) having different percentages of Mg (determined from elemental distribution image).

Figure 5:
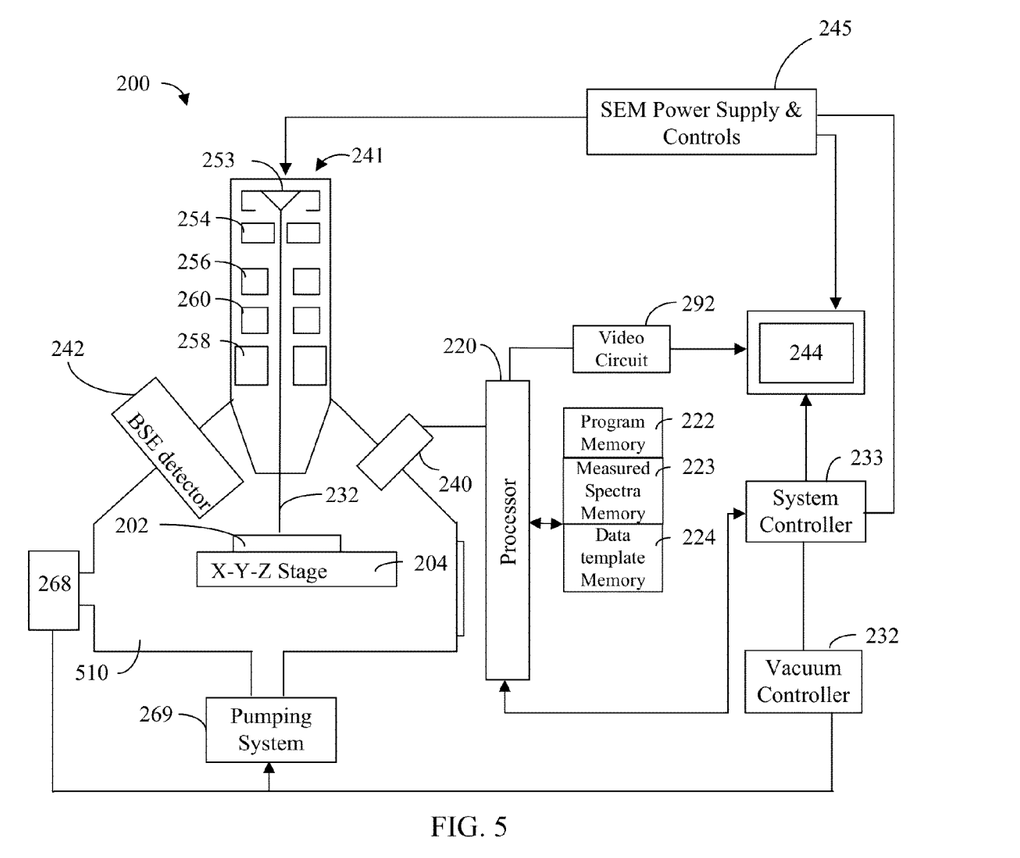
FIG. 5 is an illustration of a mineral identification and analysis system.

FIG. 5 is an illustration of a mineral identification and analysis system 200. The mineral identification system 200 includes a scanning electron beam system 241, an x-ray detector 240, and a secondary or backscatter electron detector 243. An electron beam 232 emitted from a cathode 253 is accelerated toward an anode 254. Electron beam 232 is subsequently focused to a fine spot by means of a condensing lens 256 and an objective lens 258, and can be deflected across a sample 202 by means of a deflection coil 260 to perform a two-dimensional raster scan of the sample. The condensing lens 256, objective lens 258, and deflection coil 260 are supplied current by a power supply 245 operated under the control of a system controller 233. The sample 202 is preferably mounted on a movable X-Y stage 204 within a lower vacuum chamber 210. The vacuum chamber 210 is evacuated to high vacuum by a mechanical pumping system 269 and an ion pump 268 operated under the control of vacuum controller 232.

When the electron beam 232 strikes the sample 202, several forms of radiation are emitted, including backscattered electrons from the electron beam 232, secondary electrons produced by interactions between the electron beam 232 and the sample, and x-rays produced by interactions between the electron beam 232 and the sample that are characteristic of the elements in the sample. The back scattered electrons are detected by an electron detector 242, which outputs a signal indicative of the flux or intensity of back scattered electrons. This signal is received by processor 220. The x-rays emitted from the sample are detected by x-ray detector 240, which preferably outputs a signal indicative of the energy of the detected x-rays. To that end, x-ray detector 240 is preferably an energy dispersive detector such as a silicon drift detector. The output signal of x-ray detector 240 can be amplified and received by processor 220. The back-scattered or secondary electrons are detected by an electron detector, such as a Processor 220 can be programmed to store, for each scanned pixel, a count of the number of back scattered electrons detected, a count of the number of x-rays detected, and a histogram counting the number of x-rays detected in each of a plurality of energy bins over some energy range. Typically, the energy range is on the order of 0-10 keV, and is subdivided into energy bins of 10-20 eV, for a total of 500 to 1000 energy bins or channels per pixel.

System 200 also includes a display 244 for displaying the results of the textural and mineral analysis and other information by way of video circuit 242; a program memory 222 for storing executable computer program code to program the processor 220, and a data memory 223/224 for storing data, such as per-pixel BSE counts, x-ray counts, and x-ray emission spectra recorded from sample 202, and a library of standardized elemental or mineral x-ray emission spectra. Program memory 222 can include computer storage media in the form of removable and/or non-removable, volatile and/or nonvolatile memory and can provide storage of computer-readable instructions, data structures, program modules and other data. Generally, the processor 220 is programmed by means of instructions stored in the various computer-readable storage media. Programs and operating systems are typically distributed, for example, on floppy disks or CD-ROMs. From there, they are installed or loaded into the secondary memory of a computer. At execution, they are loaded at least partially into the computer's primary electronic memory. The invention described herein includes these and other various types of computer-readable storage media when such media contain instructions or programs for implementing the steps described above in conjunction with a microprocessor or other data processor. The invention also includes the computer itself when programmed according to the methods and techniques described herein.

While the embodiment shown uses a scanning electron microscope to generate x-rays from sample 202, other embodiments could employ a transmission electron microscope or a scanning transmission electron microscope. An x-ray fluorescence system could also be used to generate x-rays from sample 202. In other embodiments, different forms of characteristic radiation emitted from the sample, such as gamma rays, may be detected.

Although much of the previous description is directed at mineral samples from drill cores, the invention could be used to prepare samples of any suitable material. The terms "work piece," "sample," "substrate," and "specimen" are used interchangeably in this application unless otherwise indicated. Further, whenever the terms "automatic," "automated," or similar terms are used herein, those terms will be understood to include manual initiation of the automatic or automated process or step.

In the following discussion and in the claims, the terms "including" and "comprising" are used in an open-ended fashion, and thus should be interpreted to mean "including, but not limited to . . . . " To the extent that any term is not specially defined in this specification, the intent is that the term be given its plain and ordinary meaning. The accompanying drawings are intended to aid in understanding the present invention and, unless otherwise indicated, are not drawn to scale. Particle beam systems suitable for carrying out the present invention are commercially available, for example, from FEI Company, the assignee of the present application.

Although the present invention and its advantages have been described in detail, it should be understood that various changes, substitutions and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A computer implemented method for blending mineralogy images, comprising:
   receiving a base layer mineralogy image and a top layer mineralogy image; and
   sequentially, via a computer processor and for each pixel in the base or top layer mineralogy images:
      determining a base layer value from the pixel in the base layer mineralogy image;
      determining a top layer value from the pixel in the top layer mineralogy image;
      determining a luminosity value from one of the base layer or top layer values;
      determining a multiply value by multiplying the base and top layer values;
      determining an overlay value by doubling the multiply value if one of the base layer or top layer values is less than a threshold, and by inverting twice the product of the inverted top layer value with the inverted bottom layer value;
      determining an image blending weight from the luminosity value; and
      determining a blended image value as a weighted average of the multiply value and the overlay value, wherein the multiply value is weighted by the image blending weight and the overlay value is weighted by the inverted image blending weight.

2. The computer implemented method of claim 1, wherein the base layer mineralogy image is a textural mineralogy image and the top layer mineralogy image is a spatial mineral distribution image.

3. The computer implemented method of claim 2, wherein the textural mineralogy image is an image of the intensity of back-scattered electrons.

4. The computer implemented method of claim 2, wherein the textural mineralogy image is an image of the intensity of generated x-rays.

5. The computer implemented method of claim 1, wherein the luminosity value is determined from the top layer value.

6. The computer implemented method of claim 1, wherein the overlay value is determined by doubling the multiply value if the top layer value is less than a threshold, and by otherwise inverting twice the product of the inverted top layer value with the inverted bottom layer value.

7. The computer implemented method of claim 1, further comprising displaying the blended image on a display device.

8. The computer implemented method of claim 1, further comprising:
receiving a mixing parameter; and
determining the image blending weight by multiplying the luminosity value by the mixing parameter.

9. A computer program product, stored on a non-transitory computer readable medium, comprising instructions operable to cause a programmable processor to:
receive a base layer mineralogy image and a top layer mineralogy image; and
sequentially, for each pixel in the base or top layer mineralogy images:
determine a base layer value from the pixel in the base layer mineralogy image;
determine a top layer value from the pixel in the top layer mineralogy image;
determine a luminosity value from one of the base layer or top layer values;
determine a multiply value by multiplying the base and top layer values;
determine an overlay value by doubling the multiply value if one of the base layer or top layer values is less than a threshold, and by inverting twice the product of the inverted top layer value with the inverted bottom layer value;
determine an image blending weight from the luminosity value; and
determine a blended image value as a weighted average of the multiply value and the overlay value, wherein the multiply value is weighted by the image blending weight and the overlay value is weighted by the inverted image blending weight.

10. The computer program product of claim 9, wherein the base layer mineralogy image is a textural mineralogy image and the top layer mineralogy image is a spatial mineral distribution image.

11. The computer program product of claim 10, wherein the textural mineralogy image is an image of the intensity of back-scattered electrons.

12. The computer program product of claim 10, wherein the textural mineralogy image is an image of the intensity of generated x-rays.

13. The computer program product of claim 9, wherein the luminosity value is determined from the top layer mineralogy image.

14. The computer program product of claim 9, wherein the overlay value is determined by doubling the multiply value if the top layer value is less than a threshold, and by otherwise inverting twice the product of the inverted top layer value with the inverted bottom layer value.

15. The computer program product of claim 9, further comprising instructions operable to cause the programmable processor to display the blended image on a display device.

16. The computer program product of claim 9, further comprising instructions operable to cause the programmable processor to:
receive a mixing parameter; and
determine the image blending weight by multiplying the luminosity value by the mixing parameter.

17. An charged particle beam apparatus, comprising:
a charged particle beam source for illuminating a portion of the sample;
at least one detector for detecting radiation emitted from the illuminated portion of the sample; and
one or more processors configured to:
generate a base layer mineralogy image and a top layer mineralogy image for the sample; and
sequentially, via a computer processor and for each pixel in the base or top layer mineralogy images:
determine a base layer value from the pixel in the base layer mineralogy image;
determine a top layer value from the pixel in the top layer mineralogy image;
determine a luminosity value from one of the base layer or top layer values;
determine a multiply value by multiplying the base and top layer values;
determine an overlay value by doubling the multiply value if one of the base layer or top layer values is less than a threshold, and by inverting twice the product of the inverted top layer value with the inverted bottom layer value;
determine an image blending weight from the luminosity value; and
determine a blended image value as a weighted average of the multiply value and the overlay value, wherein the multiply value is weighted by the image blending weight and the overlay value is weighted by the inverted image blending weight.

18. The computer implemented method of claim 1, wherein the base layer mineralogy image is an elemental distribution image of a sample and the top layer mineralogy image is a spatial mineral distribution image of the sample.

19. The computer implemented method of claim 18, wherein determining the blended image value further comprises determining whether the base layer value is less than an elemental threshold value; and rendering the blended image value to a black value if the base layer value is less than the elemental threshold value.

20. The computer program product of claim 9, wherein the base layer mineralogy image is an elemental distribution image of a sample and the top layer mineralogy image is a spatial mineral distribution image of the sample.

21. The computer program product of claim 9, wherein the instruction to determine the blended image value further comprises instructions to determine whether the base layer value is less than an elemental threshold value; and instructions to render the blended image value to a black value if the base layer value is less than the elemental threshold value.

22. The charged particle beam apparatus of claim 17, wherein the base layer mineralogy image comprises an elemental distribution image of the sample and the top layer mineralogy image comprises a spatial mineral distribution image of the sample.

* * * * *